(12) United States Patent
Son et al.

(10) Patent No.: US 7,052,722 B2
(45) Date of Patent: May 30, 2006

(54) COMPOSITION FOR WEIGHT REDUCTION COMPRISING WATER-SOLUBLE LOW-MOLECULAR WEIGHT CHITOSAN AND HIBISCUS EXTRACT

(75) Inventors: Jong Wook Son, Seoul (KR); Jin Hee Lee, Seoul (KR); Jae Kag Lim, Seoul (KR); Kang Pyo Lee, Seoul (KR)

(73) Assignee: CJ Corp., Seoul (KR)

( * ) Notice: Subject to any disclaimer, the term of this patent is extended or adjusted under 35 U.S.C. 154(b) by 167 days.

(21) Appl. No.: 10/725,324

(22) Filed: Dec. 1, 2003

(65) Prior Publication Data

US 2005/0118294 A1    Jun. 2, 2005

(51) Int. Cl.
*A61K 35/78* (2006.01)
*A01N 43/04* (2006.01)

(52) U.S. Cl. ........................... 424/725; 514/55

(58) Field of Classification Search ................ 424/725, 424/778; 514/55, 909
See application file for complete search history.

(56) References Cited

U.S. PATENT DOCUMENTS

| 5,976,550 | A  | * | 11/1999 | Engel et al. ................. 424/734 |
| 6,326,475 | B1 | * | 12/2001 | Angerer et al. ............... 536/20 |
| 6,426,077 | B1 | * | 7/2002  | Grace et al. ................. 424/400 |
| 6,780,851 | B1 | * | 8/2004  | Cavazza ....................... 514/55 |
| 2004/0076690 | A1 | * | 4/2004 | Ikemoto et al. .............. 424/729 |
| 2004/0185069 | A1 | * | 9/2004 | Gupta ........................ 424/401 |

FOREIGN PATENT DOCUMENTS

| CN | 1245060   | * | 2/2000  |
| CN | 1318317   | * | 10/2001 |
| JP | 04108734  |   | 4/1992  |
| JP | 62184002  | * | 8/1997  |
| KR | 2001 0103065 | * | 11/2001 |
| KR | 0103065   |   | 11/2001 |
| KR | 0085981   |   | 11/2002 |
| KR | 0056753   |   | 7/2003  |
| RU | 2215424   | * | 11/2003 |

* cited by examiner

*Primary Examiner*—Christopher R. Tate
(74) *Attorney, Agent, or Firm*—Arent Fox PLLC

(57) ABSTRACT

The present invention relates to compositions for weight reduction, comprising a water-soluble low-molecular weight chitosan and a Hibiscus extract, and optionally L-carnitine, and methods of using the composition for weight reduction.

4 Claims, No Drawings

COMPOSITION FOR WEIGHT REDUCTION COMPRISING WATER-SOLUBLE LOW-MOLECULAR WEIGHT CHITOSAN AND HIBISCUS EXTRACT

BACKGROUND OF THE INVENTION

The present invention relates in general to a composition for weight reduction. More particularly, the present invention relates to a composition for weight reduction, comprising a water-soluble, low-molecular weight chitosan and a Hibiscus extract, and optionally, L-carnitine.

Obesity is known to be significantly correlated with the onset of various diseases in adults. In particular, obesity onset leads to the prevalence of diabetes, cholelithiasis, hypertension, heart diseases and cerebral apoplexy. The most rational method for treating obesity is to ingest only essential nutrients and limit caloric intake.

However, typically, such caloric-restricted diets severely limit the intake of food, causing an increase in one's desire for food intake after weight reduction.

Effective weight reduction can be achieved by both decreased caloric intake and increased caloric expenditure, resulting in reduced body fat accumulation. There is a need for a realistic method of weight reduction based on the control of caloric intake with the support of a functional aid, for example, by using a functional food capable of treating obesity and offering balanced nutrient intake without undesired side effects.

In order to induce an effective anti-obesity effect, the functional food used for body weight reduction should be capable of suppressing dietary fat absorption, promoting degradation of accumulated adipose tissue and inhibiting synthesis of body fat from nutrients derived from excessive sugars. Functional food products currently used in weight reduction comprise food ingredients having varying identified efficacies, which are simply mixed. Many of these products are ineffective and do not have ingredients which work synergistically. Furthermore, the effects of the ingredients can be reduced and severe side effects can arise from its use.

SUMMARY OF THE INVENTION

The present invention relates to compositions for weight reduction. The composition of the present invention comprise water-soluble, low-molecular weight chitosan and a Hibiscus extract, and optionally, L-carnitine. The present invention further relates to methods of using the composition in weight reduction.

The present invention is based on the discovery that the presently claimed composition, when administered to overweight human subjects, is an effective agent in inducing weight loss and do not cause any undesired side effects, such as nutritional deficiency, increased blood pressure, diarrhea, constipation, insomnia and apprehension. The present composition is more effective in reducing body weight, even in low concentrations, when compared to the use of the components of the compositions when used alone. Furthermore, the mixture was found to have a synergistic effect on the reduction of body fat, including intestinal fat.

DETAILED DESCRIPTION OF THE INVENTION

In an aspect, the present invention relates to a composition for weight reduction, comprising a water-soluble, low-molecular weight chitosan and a Hibiscus extract.

Conventional chitosan is a poor agent in fat absorption, because it cannot be solubilized at the neutral pH conditions of the intestine. To solve the solubility problem, chitosan is partially digested with an enzyme to produce chitosan with various molecular weights. Chitosan having an average molecular weight of 2,000 Da to 20,000 Da is selectively collected by ultrafiltration, and used in the presently claimed composition for weight reduction.

Chitosan, or β-1,4-poly-glucosamine, produced by deacetylation of chitin derived from the shells of crustaceans, is non-toxic and displays the desired properties of absorptivity, moisturizing property, emulsifiability and biodegradability. Also, chitosan is known to have various therapeutic functions, including antimicrobial activity, deacidification activity, anti-ulcer activity, cholesterol and neutral lipid reducing activity, antitumor activity, promotion of growth intestinal bacteria, activation of plant cells and restoration of the immune response.

Sugano et al. first reported the use of chitosan to reduce blood cholesterol level. Many researchers have since reported that chitosan, when orally administered to mouse and human subjects, increases the secretion of bile acid in the intestine, and reduces blood cholesterol levels. Its cholesterol-reducing effect is believed to be related to chitosan's role as a dietary fiber, having multivalent cationic properties in solution and molecular weight.

The chitosan contained in the composition of the present invention is preferably an edible chitosan (β-1,4-poly-glucosamine) that is water-soluble at a neutral pH or a weak alkaline conditions and has an average molecular weight of 2,000 Da to 20,000 Da. This low-molecular weight chitosan may be prepared, for example, by a method disclosed in Korean Patent Laid-open Publication No. 2002-0085981. The chitosan is prepared by dissolving in an organic acid chitosan produced by deproteination and deacetylation of chitin, partially digesting the chitosan with an enzyme that destroys chitosan and collecting chitosan with a molecular weight of 2,000 Da to 20,000 Da by ultrafiltration. This application discloses a cholesterol-reducing agent comprising chitosan obtained by the method as described above in combination with ε-polylysine. Japanese Patent Laid-open Publication No. Heisei. 4-108734 also describes the use of low-molecular weight chitosan as a cholesterol-reducing agent. However, the aforementioned publications describe only the cholesterol-reducing effect of the low-molecular weight chitosan, with no disclosure of its effect on body weight reduction.

Therefore, the present invention preferably relates to a composition for weight reduction, comprising a water-soluble chitosan with a molecular weight of 2,000 Da to 20,000 Da and a Hibiscus extract.

Based on the total weight of the composition of the present invention, the content of the chitosan ranges from 5 to 95% by weight, and preferably, 20 to 60% by weight, and the content of the Hibiscus extract ranges from 5 to 95% by weight, and preferably, 20 to 60% by weight.

The Hibiscus extract contained in the composition of the present invention is an extract of petals from a Hibiscus plant, and contains hibiscus acid ((+)-allo-hydroxy citric acid, lactone form). The extract derived from Hibiscus is known to increase urination, and have antihypertensive and antibacterial properties.

Laid-open Korean Publication No. 2003-0056753 discloses a composition comprising a powdered extract from Shiitake mushroom mycelia, a powdered extract from *Agaricus* mushroom mycelia and a water-soluble chitosan powder as essential ingredients, and a powdered Hibiscus extract as an auxiliary ingredient. The composition is based on the finding that the two kinds of mushroom mycelia and chitosan have no effects on weight reduction when used separately, but are effective in reducing body weight when used in combination at a specific ratio. However, the application does not describe a particular limitation for the water-soluble chitosan powder.

Korean Pat. Laid-open Publication No. 2001-0103065 discloses a composition for weight reduction, comprising a dietary fiber selected from powdered Psyllium seed husks, galactomanan, glucomanan and beet fiber as an essential ingredient, and a *Garcinia cambogia* extract, a Hibiscus extract, *cascara sagrada* and a *Camellia sinensis* (green tea) extract as auxiliary ingredients. The Laid-open publication No. 2001-0103065 discloses Hibiscus extract as an auxiliary ingredient used in an amount of 11 to 13 parts by weight, based on the total weight of the composition. Use of the Hibiscus extract beyond the disclosed range in the composition does not produce a desired effect in weight reduction.

In a preferred aspect, the composition of the present invention may further comprise L-carnitine in an amount of 5 to 100% by weight, and preferably, 30 to 70% by weight, based on the weight of the chitosan.

L-carnitine is a compound isolated from a meat extract by Gluwitsch and Krimberg in 1905. In 1959, Fritz found that carnitine promotes the oxidation of long-chain fatty acids. Since then, studies associated with carnitine have been focused on its behavior and action in the myocardium on ischemic heart diseases.

Preferably, the composition of the present invention may comprise 30 to 70% by weight of chitosan, 15 to 50% by weight of a Hibiscus extract and 15 to 50% by weight of L-carnitine.

More preferably, the composition may comprise 35 to 65% by weight of chitosan, 15 to 40% by weight of a Hibiscus extract and 15 to 40% by weight of L-carnitine. Most preferably, the composition may comprise 40 to 60% by weight of chitosan, 20 to 35% of a Hibiscus extract and 20 to 35% by weight of L-carnitine.

In addition to the above ingredients, the composition of the present invention may further comprise additional ingredients, for example, water-soluble edible fibers.

The composition of the present invention may be administered via various routes, for example, orally, parenterally, etc., and formulated into tablets, capsules, injectable preparations, etc. The dosage of the composition is an effective amount capable of obtaining a weight reduction effect, and may be easily determined by one skilled in the art.

As shown in Examples 1–3, the presently claimed composition induces weight reduction in subjects when administered. Components of the composition of the present invention have no weight reduction effect or have a low weight reduction effect when used independently. However, when used simultaneously, they exhibit a synergistic effect on weight reduction, thus leading to effective weight reduction.

The composition of the present invention was orally administered for 8 weeks to overweight adult women not having other diagnosed diseases, and caused their body fat percentage to be reduced by 5.6%, accompanied by a reduction of body weight, with no adjustment in caloric intake and expenditure. As a result of computed tomography (CT scans), the abdominal visceral fat area at L4 level was significantly reduced by 8.6%. In addition, during the clinical test period of 8 weeks, the subjects reported high compliance rates, and there was no report of side effects. Further, serum lipid and lipoprotein concentrations were not changed.

Therefore, in case of applying dietary supplementary ingredients to overweight persons aiming to reduce body weight and body fat, by combinational administration rather than separate administration, they can have a significantly improved effect on weight reduction even in relatively low concentrations. In addition, such an effect can be augmented when they are used together with controlled caloric intake.

The present invention will be explained in more detail with reference to the following examples. However, the following examples are provided only to illustrate the present invention, and the present invention is not limited to them.

EXAMPLE 1

Preparation of Water-soluble Low-molecular Weight Chitosan

Chitosan was mixed with distilled water in a ratio of 9.5:1 to give a 5.0% solution in an extraction tank with agitation. During the dissolution of chitosan in water, the mixture was adjusted to pH 5.0 with use of lactic acid, and the temperature of the mixture was adjusted to 40° C.

After being dissolved in water, chitosanase was added to the tank in an amount of 3.0 U/g chitosan, based on the weight of the added chitosan. The chitosan degradation reaction was carried out with agitation at 10 rpm for about 5 hrs.

In order to recover only chitosan with the desired molecular weights, the degraded chitosan was subjected to ultrafiltration. Size fractionation was carried out using ultrafilter membranes, and thus fractions with the desired molecular weights were collected.

The residual salts and compounds responsible for odor were removed by absorption to an anionic exchange resin.

The eluate was concentrated under vacuum in a rotatory evaporator up to a desired solid matter concentration.

The concentrate was freeze-dried in a freez-drying pan. Also, the concentrate was reduced to powder by drying under vacuum and spray-drying.

An average molecular weight of chitosan prepared as described above was determined by GPC (gel permeation chromatography) under the following conditions:

Analysis system: Waters HPLC-GPC;

Column: Ultrahydrogel 250 GPC column (MW 1,000–80,000);

Developing solvent: 0.1M NaCl in 0.2% acetic acid;

Flow rate: 0.3 ml/min;

Detector: RI detector;

Injected amount of sample: 15 μl; and

Standard: Dextran with molecular weights of 8,000, 11,500, 40,500 and 69,500.

As a result, the prepared chitosan was found to have an average molecular weight of 15,000. Also, 80% of the prepared chitosan was found to have a molecular weight of 2,000 Da to 20,000 Da.

EXAMPLE 2

Preparation of Composition for Weight Reduction

EXAMPLE 2.1

Chitosan prepared in Example 1, a Hibiscus extract obtained from Sensient (Germany) and L-carnitine obtained from Biosint (Italy) were mixed according to the composition listed in Table 1, below, and then filled into 450 mg hard capsules.

TABLE 1

| Ingredient | Content % | Remarks |
|---|---|---|
| Water-soluble chitosan | 53 | Average MW: 2,000–20,000 |
| Hibiscus extract | 18 | HCA content: ≧ 30% |
| L-carnitine | 29 | L-carnitine content: ≧ 90% |

EXAMPLE 2.2

Chitosan prepared in Example 1, a Hibiscus extract and L-carnitine were mixed in an amount of 45%, 25% and 30% by weight, respectively, and then filled into 450 mg hard capsules.

EXAMPLE 2.3

Chitosan prepared in Example 1, a Hibiscus extract and L-carnitine were mixed in an amount of 55%, 24% and 21% by weight, respectively, and then filled into 450 mg hard capsules.

EXAMPLE 2.4

Chitosan prepared in Example 1, a Hibiscus extract and L-carnitine were mixed in an amount of 48%, 30% and 21% by weight, respectively, and then filled into 200 mg hard capsules.

EXAMPLE 2.5

Chitosan prepared in Example 1, a Hibiscus extract and L-carnitine were mixed in an amount of 44%, 21% and 35% by weight, respectively, and then filled into 200 mg hard capsules.

EXAMPLE 3

Assay for Body Weight-reducing Effect of the Composition of the Present Invention by Clinical Test The composition of the present invention was evaluated for body weight-reducing effect by a clinical test.

EXAMPLE 3.1

Selection of Subjects and Administration of the Composition of the Present Invention This clinical test was carried out with 50 pre-menopausal overweight women, who have an initial percent ideal body weight (PIBW) of greater than 110%. Before volunteering for the clinical test, the subjects sufficiently understood the test period, test objects and methods, rules to be observed, expected effects, and the like, and signed a written consent for this clinical test. The subjects were healthy women with no diagnosed diseases or disorders, with the exception of a weight problem.

The subjects were randomly divided into four groups, and a double blind test was then carried out. A test group was administered with hard capsules prepared in Example 2.1, which contained the composition of the present invention. A control group was administered with hard capsules containing 100% dextrin. Two capsules were administered 30 min before a meal for 8 weeks. Prior to start of the tests, there was no difference between the test and control groups with regard to body mass index and serum lipid concentration. There were 24 subjects in the test group and subjects in the control group with the completion of the clinical test.

EXAMPLE 3.2

Recording of Food Intake and Physical Activity

For each subject, height and body weight were measured by anthropometric measures, and percentage ideal body weight (IBW) was calculated by dividing actual body weight (kg) with 0.9 [(height(cm)−100)×0.9]. Percentage body fat (% body fat) and lean body mass (LBM) were measured directly using the Body fat analyzer TBF-105 (Tanita Co., Japan). In addition, with each subject standing up on a flat floor, the circumference of their waist and hips was measured using a tape, and the resulting waist to hips circumference ratio (WHR) was used as a marker for abdominal obesity. At the same time as collecting blood samples, blood pressure was measured using an automatic blood pressure monitor after putting each subject at ease for over 10 min.

Right before the clinical test was started, food intake was recorded by the 24-hour recall method, and daily total caloric intake (TCI) was analyzed with the N3 Program (N-squared Co Ltd, OR, USA) in which the Korean food composition table was used. Also, for each subject, the basal metabolic rate (BMR) was calculated by the Harris-Benedict equation, and daily total energy expenditure (TEE) was determined, taking into consideration physical activity levels recording physical activity for 24 hrs. In addition, in order to investigate food intake and physical activity after administration of the capsules, food intake and physical activity were recorded for the last three days of this clinical test.

EXAMPLE 3.3

Measurement of Serum Lipid and Lipoprotein Levels

Using blood samples collected from each subject before a meal, serum total cholesterol and neutral fat levels were enzymatically measured by using the Auto Chemistry Analyzer Express Plus (Chiron Diagnostics Co, MA, USA). High density lipoprotein (HDL) cholesterol level was estimated by precipitating chylomicron, low density lipoprotein (LDL) and very low density lipoprotein (VLDL) with a precipitating agent and measuring again cholesterol level in HDL presenting in the resulting supernatant by an enzymatic assay. The LDL cholesterol level was calculated by the Frideman equation, and atherogenic index (AI) was designated by (total cholesterol level −HDL cholesterol level)/HDL cholesterol level. The serum concentrations of apolipoproteins A1 and B were determined by treating the apolipoprotein sample with a specific anti-serum to insoluble complexes and then turbidimetrically measuring absorbance at 340 nm using the Immunoturbidimetric analyzer (Cobas Integra Roche, Swizerland).

EXAMPLE 3.4

Measurement of Body Fat and Muscle Area by CT Scanning

CT (computed tomography) scanning was performed with a Hispeed Advantage CT scanner (GE Medical System, WI, USA). Total abdominal fat area was determined by scanning the cross-sectional area at lumber spine L1 and L4 by CT scanning and then analyzing an area having a Hounsfield number ranging from −150 to −50. Using the peritoneum of the abdomen and the back as the boundary, the visceral fat area was determined from the inner region of the boundary, and subcutaneous fat area was calculated from the outer region of the boundary. From a cross-sectional area of the mid portion of upper border of patella and greater trochanter, the thigh muscle area was measured by determining an area having a Hounsfield number ranging from −49 to +100, and thigh fat area was measured by determining an area having a Hounsfield number ranging from −150 to −50. Muscle area per unit weight (cm/kg body weight) was calculated by dividing the thigh muscle area with total body weight.

EXAMPLE 3.5

Statistical Analysis

Data collected were introduced to the SPSS package 11.0 (Statistical Package for the Social Science, SPSS Ins, Chicago, Ill., USA), and all results were designated as mean±SE. The paired t-test was used to compare a same group, and the student t-test was performed to compare the initial values of the data between the test group with the control group, as well as to compare the data in each group collected before and after administration of the composition formulated into capsules of the present invention. In all analyses, p values less than 0.05 were considered significant. The results are described herein in detail as follows:

EXAMPLE 3.6

Change in Body Weight and Body Fat

There was no significant difference between the test and control groups for initial body mass index and age. No change in body weight and body fat was observed in the control group after the eight weeks. In contrast, in the test group, body weight was significantly decreased from 66.7±1.6 kg to 65.6±1.5 kg, and body fat was effectively reduced by about 5.6% (39.1±1.0% vs 36.9±1.0%). In addition, when comparing the change in % body fat in each group during the clinical test period of 8 weeks, body fat percentage (% body fat) in the test group was significantly decreased (p=0.013). Muscle mass was found to slightly increase (40.5±0.8 vs 41.2±0.8), and blood pressure was not significantly different in both systolic pressure and diastolic pressure for the test group.

With regard to food intake and physical activity before and after administration of the composition of the present invention, the total caloric intake of the control group was slightly increased, and the basal metabolic rate of the test group was decreased after 8 weeks of administration. It seems to be due to the reduction of body weight of the test group. But, after 8 weeks, the total energy expenditure of two groups was not changed, and the total caloric intake did not show a difference when compared to the initial total caloric intake.

EXAMPLE 3.7

Abdominal Fat Area by CT Scanning

Analysis of abdominal fat area by CT scanning at the level of L1 and L4 vertebra showed no significant difference between the control group and the test group in the initial total fat area, abdominal visceral fat area and abdominal subcutaneous fat area, prior to start of clinical test. After administration of the composition, visceral fat area and subcutaneous fat area were not changed in either the control or test groups at the L1 vertebra. Specifically in the test group, the visceral fat area at the level of L1 was not changed after administration of the composition of the present invention. Although the subcutaneous fat area was slightly decreased after administration of the presently claimed composition for the test group, it was not a significant difference.

In the test group administered with the composition of the invention, the visceral fat area at the level of L4 was significantly decreased by about 8.6% (104.5±6.6 $cm^2$ vs 95.5±6.6 $cm^2$, p=0.008). At the level of L4, the subcutaneous fat area was not changed (221.2±12.2 $cm^2$ vs 222.5±12.8 $cm^2$). Thus, at the level of L4 vertebra, total fat area was decreased by about 2.4% (325.7±14.7 $cm^2$ vs 318.0±14.9 $cm^2$, before and after administration of the composition of the present invention, respectively (p=0.051). Since the amount of the visceral fat area was decreased, the resulting ratio of visceral fat area to subcutaneous fat area was improved significantly (0.50±0.04 vs 0.46±0.05, p=0.039). In addition, in the level of L4, both the ratio of visceral fat area to thigh muscle area (p=0.002) and the ratio of visceral fat area to thigh fat area (p=0.003) were changed significantly. With respect to muscle and fat areas of the thigh and calf, there was no difference in either group before and after administration of the composition of the present invention.

EXAMPLE 3.8

Change in Serum Lipid and Lipoprotein Levels

There was no significant difference between the test and control groups with regard to serum lipid levels. After administration of the composition over 8 weeks, the serum neutral fat level was decreased by about 10.0% (132.0±12.5 mg/dl vs 118.8±11.6 mg/dl, p=0.023) in the test group. In the control group, the serum neutral fat level was slightly increased, but the results were not significant. Serum total cholesterol level was, in the test group, decreased by about 2.7% (193.7±6.3 mg/dl vs 188.5±6.2 mg/dl), but the results were not significant (p=0.159). In both groups, there was no difference in LDL cholesterol levels and apolipoprotein B levels before and after administration of the composition of the present invention. Also, there was no difference in HDL cholesterol levels and apolipoprotein A1 levels. In the test group, the atherogenic index was decreased, but not significant, while there was no difference in the ratio of total cholesterol levels to HDL cholesterol levels and the ratio of LDL cholesterol levels to HDL cholesterol levels.

Among the 24 subjects in the test group, eight cases (33.3%) were found to have a serum total cholesterol level greater than 200 mg/dl, five cases (20.8%) had a LDL cholesterol level greater than 130 mg/dl, and six cases (25.0%) had a serum neutral level greater than 160 mg/dl. Based on these results, 10 subjects (41.7%) were identified to have hyperlipidemia, who have a serum total cholesterol level greater than 200 mg/dl, a LDL cholesterol level greater than 130 mg/dl, or a serum neutral fat level greater than 160 mg/dl. The test groups were classified into a normal group and a hyperlipidemia group. When comparing the effect of the composition of the present invention on serum lipid or cholesterol level, there was no significant difference between the two groups.

The invention claimed is:

1. A composition for weight reduction, comprising a water-soluble chitosan having a molecular weight of between 2,000 Da and 20,000 Da,1 a Hibiscus extract and L-carnitine, wherein the composition comprises 30 to 70% by weight of chitosan, 15 to 50% by weight of a Hibiscus extract, and 15 to 50% by weight of L-carnitine.

2. The composition of claim 1, wherein the composition comprises 53% by weight of chitosan, 18% by weight of a Hibiscus extract, and 29% by weight of L-carnitine.

3. A method of inducing weight reduction in a subject comprising administering to said subject a composition comprising a water-soluble chitosan having a molecular weight of between 2,000 Da and 20,000 Da, a Hibiscus extract and L-carnitine, wherein the composition comprises 30 to 70% by weight of chitosan, 15 to 50% by weight of a Hibiscus extract and 15 to 50% by weiaht of L-carnitine in an amount sufficient to produce a reduction in weight of the subject.

4. The method of claim 3, wherein the composition comprises 53% by weight of chitosan, 18% by weight of a Hibiscus extract, and 29% by weight of L-carnitine.

* * * * *